United States Patent [19]

Johnson et al.

[11] Patent Number: 6,129,766
[45] Date of Patent: Oct. 10, 2000

[54] PROSTHETIC FOOT ASSEMBLY HAVING IMPROVED RESILIENT CUSHIONS AND COMPONENTS

[75] Inventors: Christopher Lyle Johnson, Plainwell; Eric Lloyd Robinson, Sterling Heights, both of Mich.

[73] Assignee: College Park Industries, Inc., Fraser, Mich.

[21] Appl. No.: 09/087,010

[22] Filed: May 29, 1998

Related U.S. Application Data

[60] Provisional application No. 60/047,932, May 30, 1997, provisional application No. 60/065,560, Nov. 14, 1997, and provisional application No. 60/065,561, Nov. 14, 1997.

[51] Int. Cl.[7] .................................................. A61F 2/66
[52] U.S. Cl. ............................................. 623/49; 623/52
[58] Field of Search .......................... 623/27, 38, 47–56

[56] References Cited

U.S. PATENT DOCUMENTS

| | | |
|---|---|---|
| 4,892,554 | 1/1990 | Robinson ................................ 623/55 |
| 5,158,570 | 10/1992 | Schey et al. ........................... 623/52 |
| 5,258,038 | 11/1993 | Robinson et al. ..................... 623/49 |

FOREIGN PATENT DOCUMENTS

1404072 A1  6/1988  U.S.S.R. .................................. 623/27

*Primary Examiner*—David H. Willse
*Attorney, Agent, or Firm*—Howard & Howard

[57] ABSTRACT

A prosthetic foot assembly, said assembly includes an ankle member, a heel member pivotally connected to the ankle member, an elongate metatarsal-toe member having a rear portion underlying a forward portion of the heel member and projecting forwardly from the heel member. The metatarsal-toe member being pivotally connected to the heel member. A first compressible element is engaged between a portion of the ankle member and a portion of the heel member and a second compressible element having first and second substantially circular bearing surfaces engaged between a portion of the heel member and a portion of the metatarsal-toe member to resist upward pivotal movement of a forward end of the metatarsal-toe member relative to the heel member. A portion of the compressible element spaced apart from one of the bearing surfaces has a smaller diameter than the diameter of at least one of the first and second bearing surfaces. Also disclosed is a prosthetic foot assembly incorporating noise abatement features including surface treatments and modified compressible elements or pads.

21 Claims, 10 Drawing Sheets

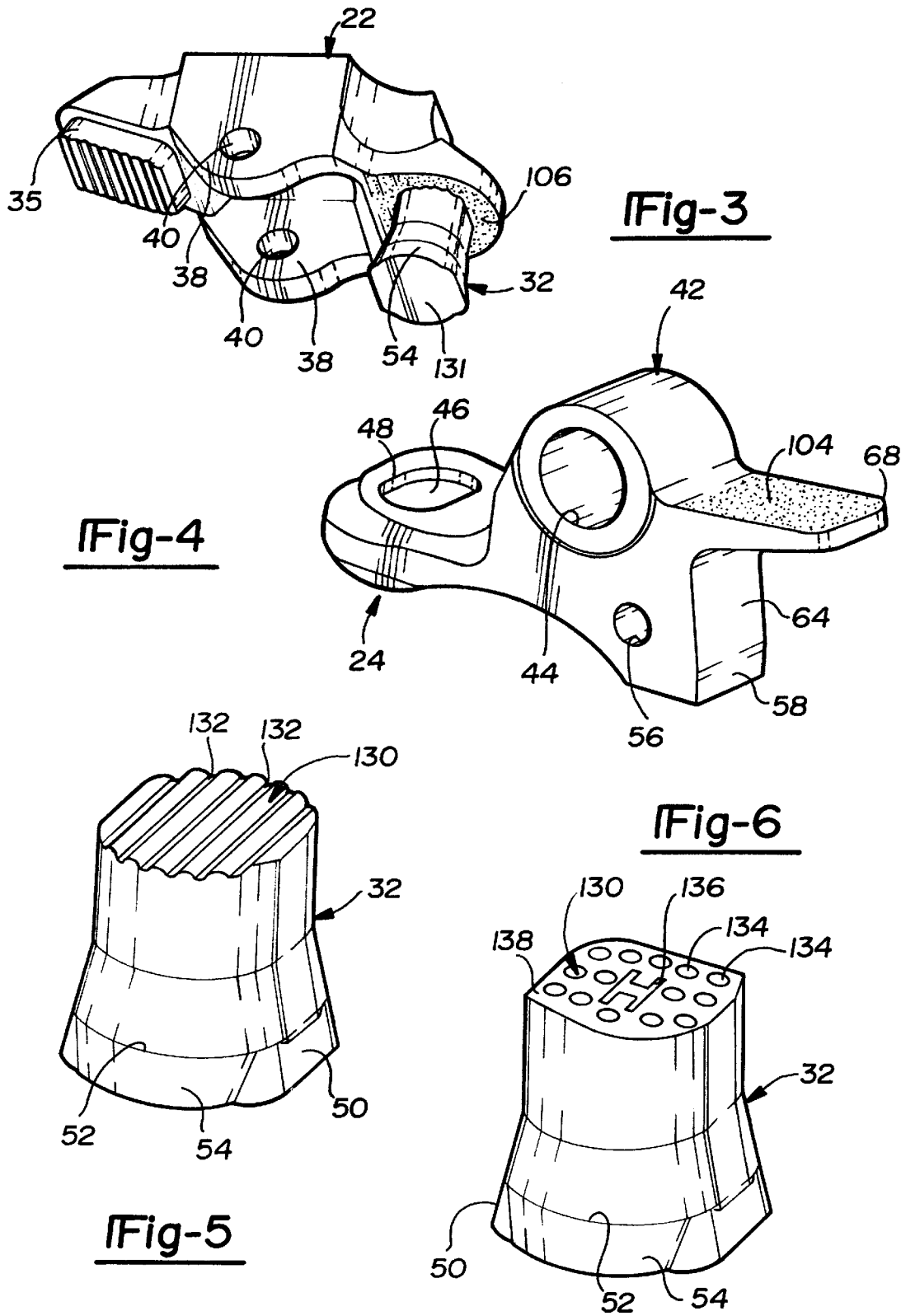

PROSTHETIC FOOT ASSEMBLY HAVING IMPROVED RESILIENT CUSHIONS AND COMPONENTS

This application claims priority to U.S. Ser. No. 60/047,932 filed May 30, 1997; U.S. Ser. No. 60/065,560 filed Nov. 14, 1997; and U.S. Ser. No. 60/065,561 filed Nov. 14, 1997.

TECHNICAL FIELD

This invention relates to prosthetic feet and, more particularly, to multi-piece prosthetic foot assemblies having improved functional properties.

BACKGROUND OF THE INVENTION

The basic requirements of an acceptable prosthetic foot are that it will provide a stable support for the amputee throughout a reasonable range of activities and permit the amputee to walk with a normal stride. To achieve this normal stride, the prosthetic foot must flex during walking as the foot continually moves through the heel-strike, foot-flat, and toe-off cycle. It must also, throughout this cycle, provide transverse stability particularly at toe-off, when the entire weight of the amputee is applied to the forward portion of the prosthetic foot. Prior art prosthetic feet typically are substantially transversely inflexible which interferes with side to side balancing when walking on uneven surfaces. Unlike the natural foot, these types with this unevenness and an unanticipated sideways tilting of the foot at toe-off results in an imbalance at a critical portion of the stride.

Amputees are no longer satisfied to sit in a wheelchair or to be content with a stilted, unnatural walking motion. An amputee often strives to duplicate physical activities which were conducted before the amputation. These activities may include rigorous physical activities such as running, playing basketball, and dancing.

In order to be commercially acceptable, prosthetic feet must duplicate the motions of the natural foot as much as possible. These motions include side to side stability at the toe section of the foot where weight can be exerted on each side of the foot. The ankle joint must have torsional flexibility transverse to the up and down motion of the ankle which pivotally lowers and raises the foot.

The added torsional motion of the joint in the artificial foot adds a degree of stress on the resilient pads located between the members of the artificial foot which are not otherwise present in a foot that has limited motion in only the up and down direction relative to pivotable raising and lowering of the foot.

Modern, high-tech, prosthetic feet strive to more accurately replicate the function the natural foot. In order to achieve this end, the designs of these artificial feet include more and more moving parts which impacts on the reliability and aesthetic properties of the prosthetic foot assemblies. Because of the unusually high loads imposed on the joints of prosthetic foot, compressive elements such as bumpers and cushions are subject to fatigue and are prone to failure. Accordingly, it would be desirable to have a bumper or cushion design which increase the reliability of a prosthetic foot assembly while decreasing the frequency of maintenance required to maintain the prosthetic foot assembly. Additionally, it would be desirable to have bumpers or cushions which not only have extended life, but have improved dynamic characteristics (user satisfaction).

Again, related to the aesthetics of prosthetic feet, amputees do not wish to call attention to themselves by making noise as they walk. Complex prosthetic foot designs, over thousands of load cycles, can commonly cause noises as the amputee walks with the prosthetic foot assembly. Even those amputees who do not wear cosmetic covers and feel comfortable with the "high-tech" look of their artificial limb components do not appreciate the noise generated by their prosthetic devices which can be a mental distraction. Accordingly, it would be desirable to have a prosthetic foot assembly in which noise can be eliminated to make the prosthetic foot assembly which is both aesthetically and functionally more pleasing to the wearer.

In attempts to make prosthetic foot assemblies which function more like a natural foot, very complex, multi-axis assemblies have been designed. However, these designs are costly and, therefore, can exclude segments of amputees from obtaining these more functional prosthetic devices. Accordingly, it would be desirable to have a more economical prosthetic foot assembly which provides many of the benefits of multi-axis prosthetic foot assemblies while having only one pivotal axis.

SUMMARY OF THE INVENTION

In accordance with one aspect of the present invention, a prosthetic foot assembly includes an ankle member pivotally connected to a heel member which is in turn pivotally connected to an elongate metatarsal-toe member about two substantially parallel axles. A compressible element having first and second substantially circular bearing surfaces is engaged between a portion of the heel member and a portion of the metatarsal-toe member to resist upward pivotal movement of a forward end of the metatarsal-toe member relative to the heel member. The compressible element has a median portion of the compressible element or bumper spaced apart from one of the bearing surfaces has a smaller diameter than the diameter of at least one of the first and second bearing surfaces.

In accordance with another aspect of the present invention, the bearing surfaces of the compressible elements engaging an engagement surface of either the ankle member and/or the heel member include at least one interrupted bearing surface in order to prevent the generation of noise from the foot assembly.

Additionally, in accordance with the present invention, the engagement surfaces of the ankle member and/or heel member can also be interrupted in order to abate noises generated between moving surfaces of the foot assembly.

In accordance with another aspect of the present invention, an adaptor assembly for attaching a prosthetic foot assembly having an ankle member, a heel member, and a metatarsal-toe member to either an endoskeleton or an exoskeleton includes an adaptor member having a top surface adapted to engage an endoskeleton or an exoskeleton and a bottom surface adapted to engage the ankle member. The adaptor member includes a primary fastener for fixation of the adaptor member to the ankle member and also includes a secondary fastener which decreases the magnitude of stress distributed to the primary fastener by preventing the back of the adaptor element from lifting away from the ankle member under loading conditions.

According to another aspect of the present invention, a prosthetic foot assembly has an ankle member which is in turn pivotally connected to a combination for feet/heel member ("a foreheel" member) about a single axle. The ankle member has two shoulder portions with apertures therethrough that are aligned with the central bore through the foreheel member to form a passage for the axle. The foreheel member includes a central portion having a central transverse bore having a limiter eccentrically disposed therein. The axle passes through two spaced resilient bushings that are positioned in the counterbores. Interposed between the two resilient bushings is a semi-rigid liner with an inner diameter size to receive the axle. The resilient bushings allow for transverse pivotal motion about the axis of the axle while the semi-rigid liner de-couples the resilient bushings from the axle allowing the axle and semi-rigid bushing to slide relative to each other.

Other objects, features and advantages of the present invention will be readily appreciated as the same becomes better understood after reading the subsequent description taken in conjunction with the accompanying drawings.

BRIEF DESCRIPTION OF THE DRAWINGS

Other advantages of the present invention will be readily appreciated as the same becomes better understood by reference to the following detailed description when considered in connection with the accompanying drawings wherein:

FIG. 3 is a perspective view from the bottom of the ankle member;

FIG. 4 is a perspective view of the heel member shown in FIG. 1;

FIG. 5 is a perspective view of an embodiment of an improved compressible element of the present invention;

FIG. 6 is another embodiment of the improved compressible element of the present invention;

DETAILED DESCRIPTION OF THE PREFERRED EMBODIMENTS

Figure 1:
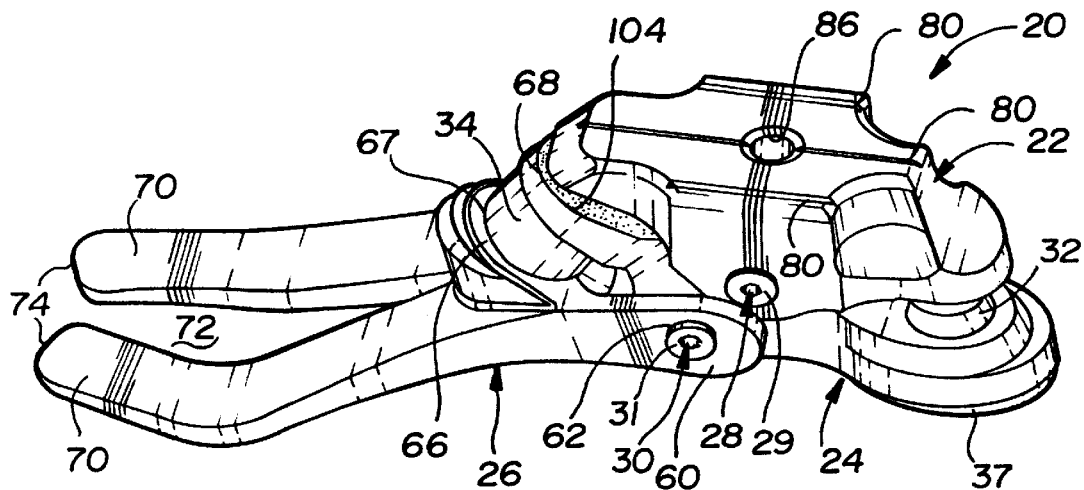
FIG. 1 is a perspective view of a prosthetic foot assembly viewed from the top in accordance with the present invention.
Figure 2:
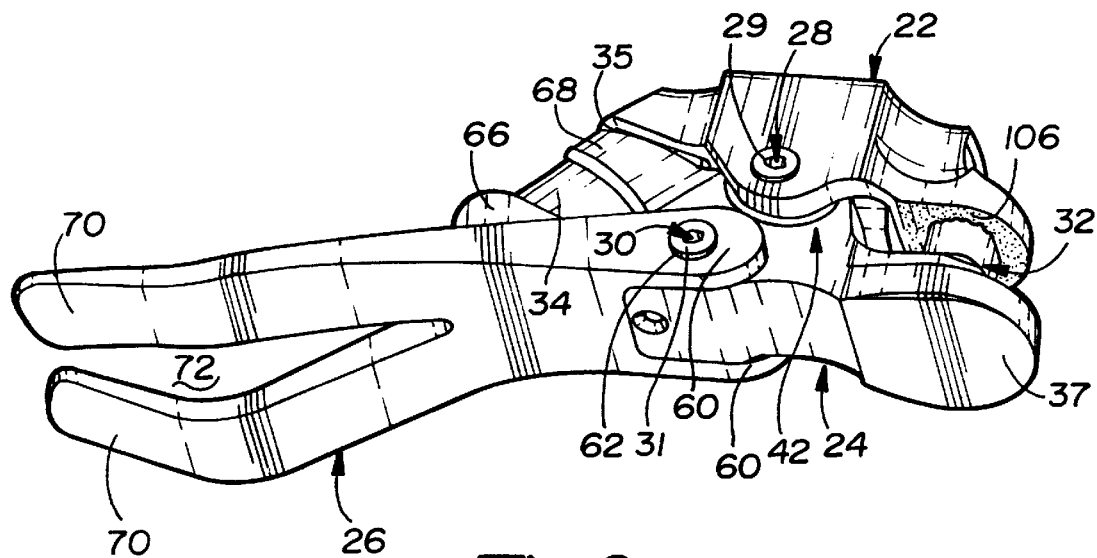
FIG. 2 is a perspective view of a prosthetic foot assembly viewed from the bottom in accordance with the present invention.

Referring to FIGS. 1 and 2, a prosthetic foot assembly 20 has an ankle member 22, a heel member 24, and a metatarsal-toe member 26. The ankle member 22 is pivotally connected to the heel member 24 through an axle joint 28. The heel member 24 is pivotally connected to the metatarsal-toe member 26 through an axle joint 30. The ankle member 22, the heel member 24, and the metatarsal-toe member 26 are made from a suitable synthetic thermoplastic or composite material such as graphite that can be fiberglass-reinforced. The axle joints 28 and 30 provide for pivotable motion of the three members along the axis of the axle joints which runs transverse to the longitudinal axis of the foot assembly 20; i.e., the length of the foot assembly 20. Furthermore, as explained below, the axle joint 28 provides for limited torsional or pivotable motion about a direction transverse to the longitudinal axis of an axle 29.

A compressible element or cushion 32 provides for resilient resistance of the heel member 24 with respect to the ankle member 22 against clockwise motion. Compressible element or cushion 34 resists upward counterclockwise motion of the metatarsal-toe member 26 with respect to the heel member 24. A mid-stance compressible element or pad 35, as best shown in FIG. 2, resists clockwise motion of the heel member 24 with respect to the ankle member 22. The compressible elements and pad 32,34,35 can be selected by size and durometer to accommodate different peoples' weight, size, and personal preferences. A heel pad 37 is bonded to the heel member 24 to absorb shock and vibration. When assembled, the foot assembly 20 can be covered by an outer layer (not shown) whose outer surface is cosmetically conformed to that of a natural foot.

Referring now to FIGS. 2, 3, and 4, the axle joint 28 includes an axle or pin 29. The ankle member 22 includes two flange sections 38, each with an aperture 40 that receives the axle 29 therein. The flanges 40 are spaced apart to receive a central portion 42 of the heel member 24. The central portion 42 has an aperture 44 which is significantly larger than the outer diameter of the axle 29. The central section 42 of the heel member 24 is received between the flanges 38 of the ankle member 22. The axle 29 passes through the apertures 40 in the flanges 38 and through the central aperture 44 to pivotally connect the ankle member 22 with the heel member 24. The general construction of the foot assembly 20 is described and shown in U.S. Pat. Nos. 4,892,554; 5,158,570; and 5,258,038 all assigned to the assignee of the present invention, and incorporated herein by reference.

Because torsional motion can exert a sideways pulling force on the compressible element 32, it is preferable that the compressible element or cushion 32 be positively engaged within the heel member 24. Referring specifically to FIG. 4, this is specifically accomplished by a recess 46 disposed in the heel member 24. The heel member 24 has a lip 48 extended over the recess 46 to positively engage the compressible element or cushion 32. As shown in FIGS. 3, 5, and 6, the compressible element or cushion 32 has a substantially oval lower section 50 with a substantially longer side 52 of the oval section 50 having a protruding ear 54 which can be received and retained in the recess 46.

Referring back to FIGS. 1 and 2, the axle joint 30 between the heel member 24 and the metatarsal-toe member 26 provides pivoting motion of the toe in an up and down direction. Referring briefly back to FIG. 4, the heel member 24 has a central aperture 56 at a lower section in proximity to an abutment shoulder 58 thereon. Referring back to FIGS. 1 and 2, the metatarsal-toe member 26 has two flanges 60 with apertures 62 therethrough that are aligned with respect to each other. The flanges 60 are spaced apart to receive a lower section 64 of the heel member 24. The aperture 56 and the apertures 62 are aligned to snugly and slidedly receive an axle or pin 31.

Referring to FIGS. 1, 2, and 4, the metatarsal-toe member 26 has a mounting section 66 which receives the compressible element or cushion 34 which abuts against a flange section 68 of the heel member 24. A portion of the compressible element or cushion 34 can be received within a recess 67 disposed in the abutment flange 68 of the heel member 24 as will be described in greater below. The compressible element or cushion 34 provides resilient resistance against the upward pivotal motion of the metatarsal-toe member 26 relative to the heel member 24.

The metatarsal-toe member 26 has two symmetrically positioned and mirror imaged toes 70 with a bifurcating slot 72 therebetween which extends from the distal ends 74 of the toes 70.

Figure 12:
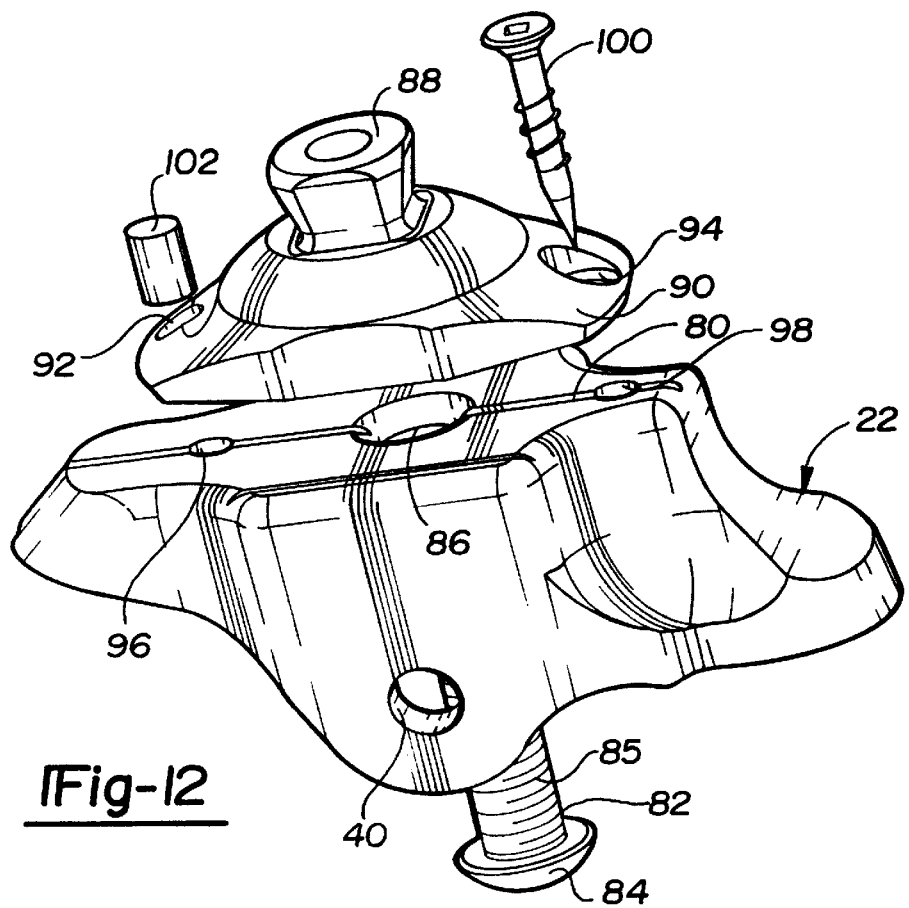
FIG. 12 is an exploded perspective view of an ankle member and adaptor assembly of the present invention.

The ankle member 22 is adaptable to be attached to either an endoskeleton or an exoskeleton as are well known in the art. Referring to FIGS. 1 and 12, the ankle member 22 has longitudinal slots 80 which non-rotatably engage standard attachments such as Otto Bock endoskeletal and exoskeletal systems and/or adaptors. The ankle member 22, however, is adaptable to be connected to any type of system.

The ankle member 22 can be attached to an adaptor 90 as shown in FIG. 12. A bolt 82 having an enlarged head 84 and threaded portion 85 passes upwardly through an aperture 86 with the head 84 of the bolt engaging the ankle member 22. The threaded portion 85 of the bolt 82 then engages a pyramid connector 88. In order to reduce the amount of stress and subsequent fatigue placed on the bolt 82, a fastener 100 is disposed in a rear aperture 94 of the pyramid connector 88 and is receivingly retained in a rear aperture 98 disposed in the ankle member 22. Additionally, an anti-rotation pin or dowel 102 can be disposed in a front aperture 92 of the adaptor 90 and is received in a front aperture 96 in the ankle member 22. The use of the fastener 100 reduces the movement of the adaptor 90 about the bolt 82 and most significantly reduces the lifting of the posterior portion of the adaptor 90 off of the surface of the ankle member 22 thus decreasing the magnitude of the stress borne by the bolt 82.

Referring to FIGS. 2, 7, 8, and 9, the mid-stance pad 35 is shown. The mid-stance pad 35 is preferably made from a resilient material such as an elastomeric material including polyurethane. The mid-stance pad 35 is disposed between a portion of the ankle member 22 and the heel member 24. The mid-stance pad 35 provides shock adsorption during dorsiflexion and allows for resisted rotation of the ankle member 22 about the heel member 24.

Figure 7:
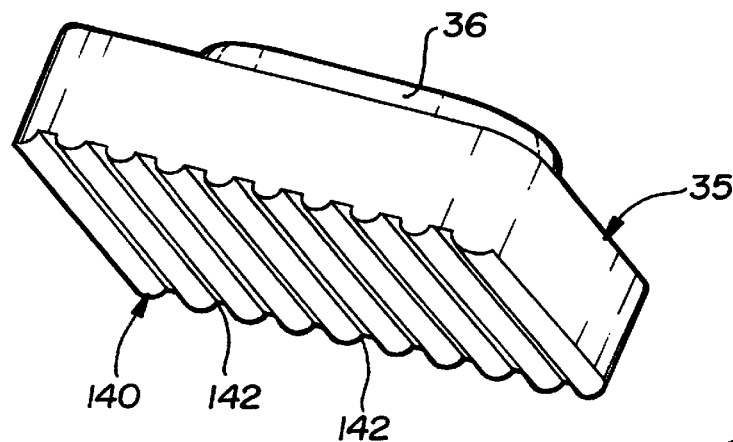
FIG. 7 is a perspective view of a mid-stance pad of the present invention.
Figure 8:
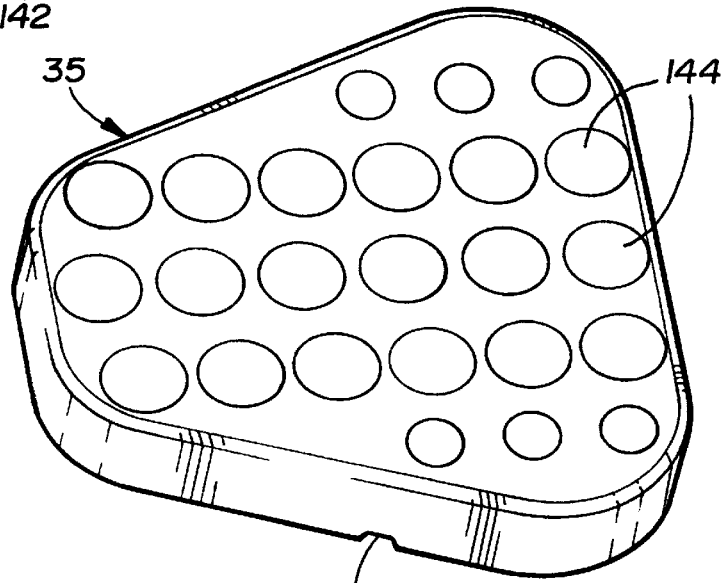
FIG. 8 is a perspective view of a further embodiment of a mid-stance pad of the present invention.

As shown in FIG. 7, the mid-stance 35 can have a generally square or rectangular shape. Preferably, as shown in FIG. 8, the mid-stance pad 35 has a "keystone" shape. The keystone-shaped pad 35 can be assembled in the foot assembly 20 with either the wider or narrower end oriented toward the anterior aspect of the foot assembly 20. That is, since the motion of the ankle member 22 and the heel member 24 is scissored closed more toward the anterior aspect of the foot assembly 20, having more material toward the anterior aspect of the foot assembly 20 creates more resistance to compression of the mid-stance pad 35 and, conversely, having less material toward the anterior aspect of the foot creates less resistance to compression of the mids-tance pad 35. Accordingly, a single mid-stance pad 35 in one durometer can satisfy the light and heavy user simply based on its orientation within the foot assembly 20.

In typical operation, the mid-stance pad 35 slides across the surface of the abutment flange 68 of the heel member 24 as shown in FIG. 4. However, if both the surface of the abutment flange and the engagement surface of the mid-stance pad 35 are smooth, noise can be generated when the mid-stance pad 35 separates from the heel member 24 or slides across the surface of the abutment flange 68 of the heel member 24. The noise is thought to be due, in part, to molecular adhesion between the material comprising the heel member 24 and the resilient material comprising the mid-stance pad 35. Additionally, noise can be caused by the sudden in-rush of air as the mid-stance pad 35 separates from the heel member 24 at heel strike. In order to eliminate, or at least minimize the production of noise at the interface of the mid-stance pad 35 and heel member 24, the surface 140 of the mid-stance pad is interrupted or discontinuous. The interrupted surface 140 can include grooves 142 disposed in the surface as shown in FIG. 7, and/or the addition of protrusions 144 and/or depressions as shown in FIG. 8. The protrusions or depressions 144 can have any geometric shape.

Figure 9:
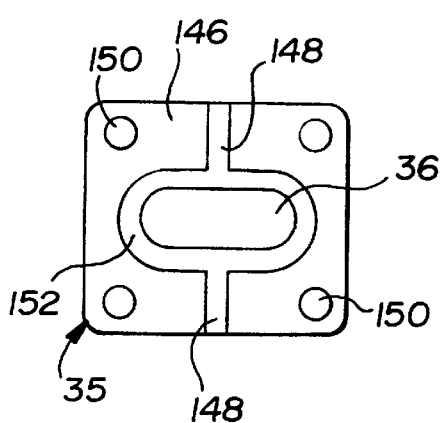
FIG. 9 is a top view of the mid-stance pad of the present invention.

Additionally, with reference to FIG. 9, the back surface 146 of the mid-stance pad 35 can include noise abatement devices. Air expulsion grooves 148 are disposed in the back surface 146 in order to allow air to escape as the mid-stance pad is compressed against the ankle member 22. Additionally, protrusions 150 can be disposed along the back surface 146 of the mid-stance pad 35 in order to interrupt the surface and allow to air to escape thus reducing the incidence of and generation of noise.

An additional groove 152 is disposed in the back surface 146 of the mid-stance pad 35 about a protuberance 36 which is used to retain the mid-stance pad 35 within the ankle member 22. In addition to channelling air from between the mid-stance pad 35 and the ankle member 22, the groove 152 reduces the stress of the material comprising the mid-stance pad 35 by eliminating the sharp transition between the protuberance 36 and the back surface 146, leading to a longer useful life for the mid-stance pad 35.

Referring to FIGS. 5 and 6, the compressible element or cushion 32 can also include an interrupted surface 130 to inhibit or prevent the generation of noise from contact with the ankle member 22. Grooves 132 can be disposed in the surface 130 as well as protrusions and/or depressions 134. Additionally, designs such as letter or numerals 136 can be utilized to not only provide specific information regarding, for example, size, durometer, etc., but can also be used to interrupt the surface 130 of the compressible element or cushion 32. Additionally, swirling, graining and/or other surface treatment can be utilized alone or in combination with any of the above mentioned mechanisms for providing an interrupted surface 130.

In addition to interrupting the surfaces 130 and 140 of the compressible element or cushion 32 and mid-stance pad 35, respectfully, the portions of the heel member 24 and ankle member 22 which contact the interrupted surfaces 130 and 140 can also be treated to reduce the generation of noise therebetween. As shown in FIGS. 1 and 4, surface 104 of the abutment flange 68 can be roughened by means such as sand-papering, grinding or other well known means of abrading known to those skilled in the art in order to provide a surface which does not generate noise in combination with the mid-stance pad 35. Referring now to FIGS. 2 and 3, surface 106 of the ankle member 22 can include roughening or abrading or other means of interrupting the surface known to those skilled in the art in order reduce the generation of noise between the compressible element 32 and ankle member 22.

Figure 10:
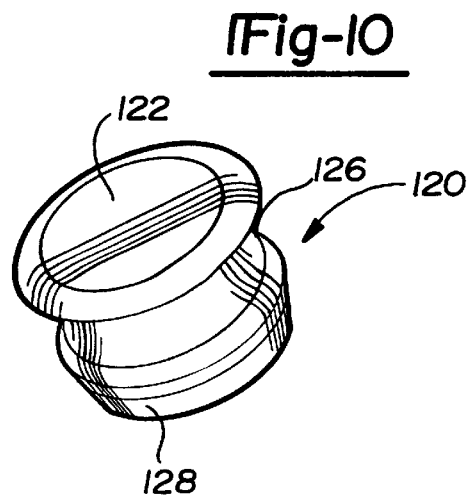
FIG. 10 is a perspective view of an improved compressible element of the present invention.
Figure 11:
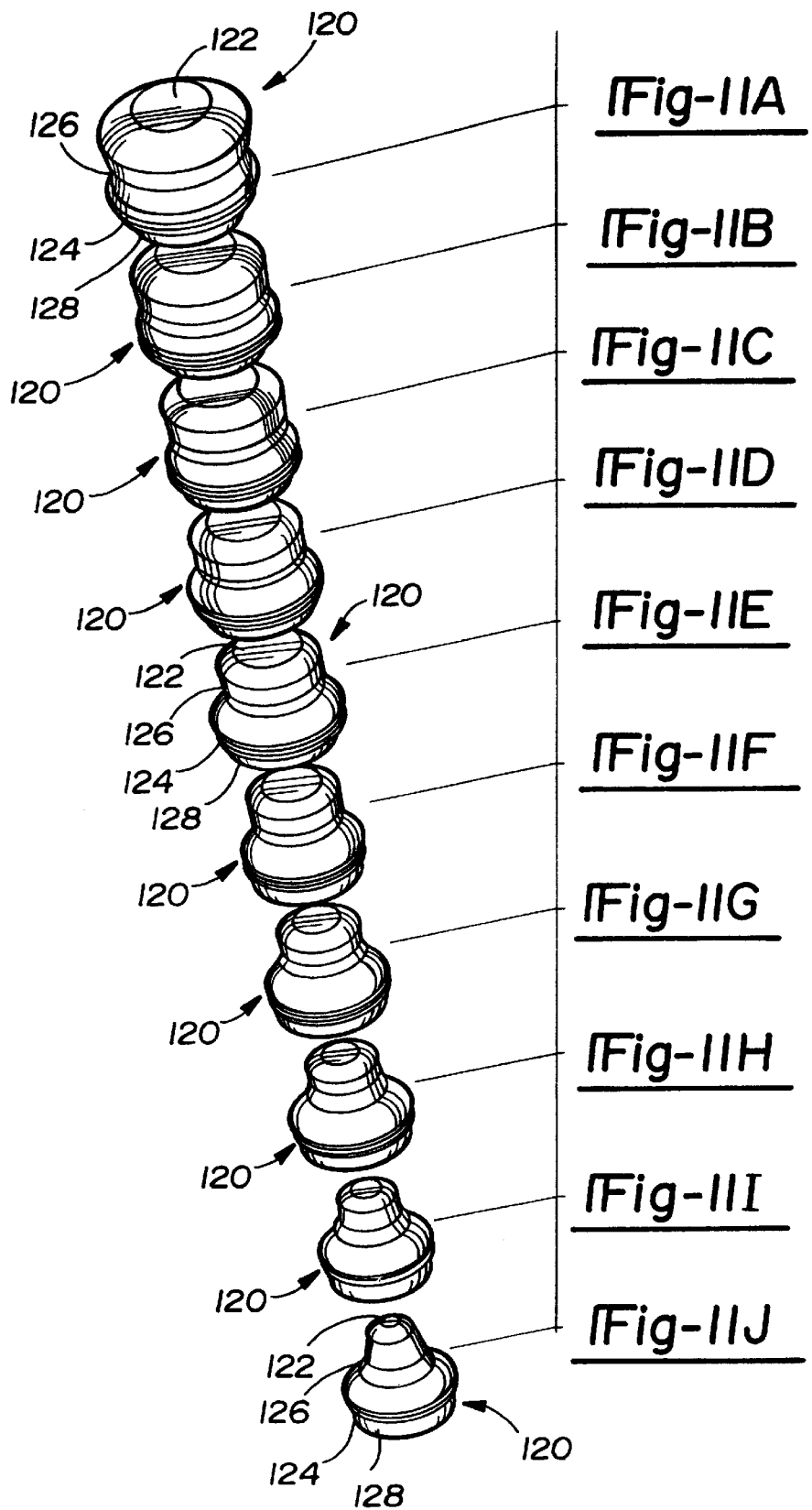
FIGS. 11A–J are perspective views of the improved compressible element of the present invention.

Referring to FIGS. 10 and 11A–J, an improved compressible element or cushion 120 is shown. The compressible element of cushion 120 can replace the element 34 as shown in FIGS. 1 and 2. The compressible element or cushion 120 includes a first substantially circular bearing surface 122 and a second substantially circular bearing surface 124 and has a region or portion 126 disposed between the bearing surfaces 122,124 which has a smaller diameter than the diameter of at least one of the first 122 and second 124 bearing surfaces. The portion 126 of the compressible element or cushion 120 which is spaced apart from the bearing surfaces 122,124 can have a diameter which is smaller than the diameter of the second bearing surface 124 and which is larger than the first bearing surface 122 as is generally shown in FIGS. 11E–11J. Alternatively, the portion 126 of the compressible element or cushion 120 can have a diameter which is smaller than the diameter of both the first bearing surface 122 and second bearing surface 124 as is generally shown in FIGS. 11A–11D. Additionally, the portion 126 can be medially disposed with respect to the first bearing surface 122 and second bearing surface 124 wherein the median portion 126 has a smaller diameter than the diameter of the first 122 and second 124 bearing surfaces as shown in FIG. 10. That is, the median region imparts an essentially "hour glass" shape to the compressible element 120 giving it enlarged rounded ends and a narrower waist. The region 126 has been found to provide better force deflection characteristics and to improve the durability of the compressive element or cushion 120 due to its ability to better handle compressive forces thereby reducing the internal stresses placed on the compressible element or cushion 120. In this way, compressive forces placed on the compressible element 120 are accommodated by the median portion 126 expanding outwardly whereas in traditional prior art bumper assemblies, the median or waist portion expands outwardly deforming the compressible element and weakening the compressible element shortening its useful life span.

Additionally, the improved compressible element or cushion 120 has a more linear compression profile yielding more natural and better feedback to the user. The compressible element 120 includes a protuberance 128 extending from the second bearing surface 124 which can be received in the recess 67 of the metatarsal-toe member 26. The compressible element 120 is preferably constructed of a resilient material such as an elastomer. The preferred elastomer being a polyurethane. A preferred material includes a low durometer (Shore A, 65) 481 AZ from Minnesota Rubber, Minneapolis, Minn. The compressible element or cushion 120 can be made by transfer molding or other well known techniques. The general idea behind the compressible element 120 is that by varying the volume, mass, diameter, and height of the compressible element or cushion 120 in a systemic way while maintaining the same basic shape, makes it possible to attain a wide range of force deflection profiles without changing the material or the basic shape of the compressible element or cushion 120.

Figure 13:
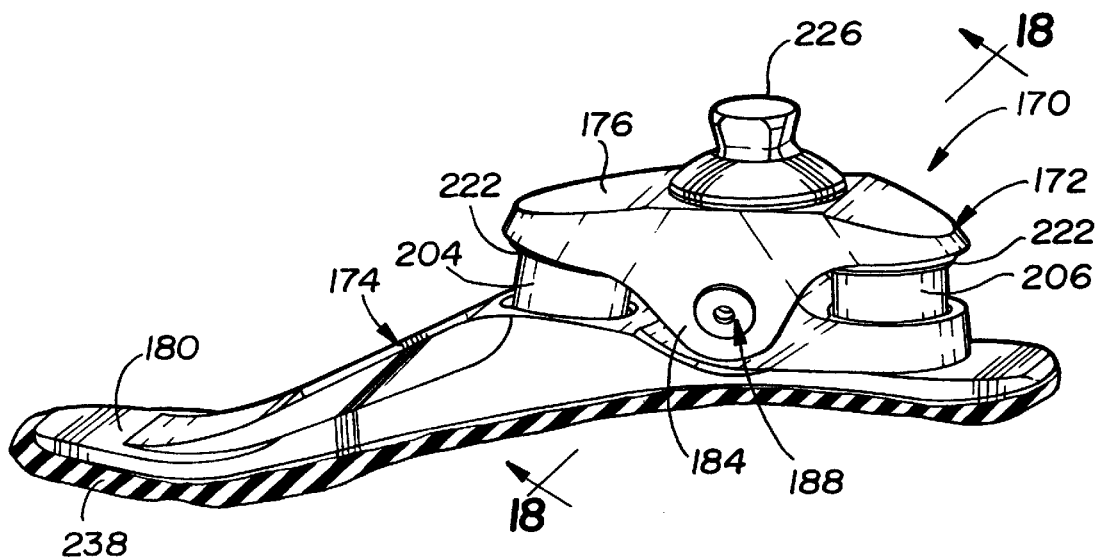
FIG. 13 is a side perspective view of an alternative prosthetic foot assembly.
Figure 14:
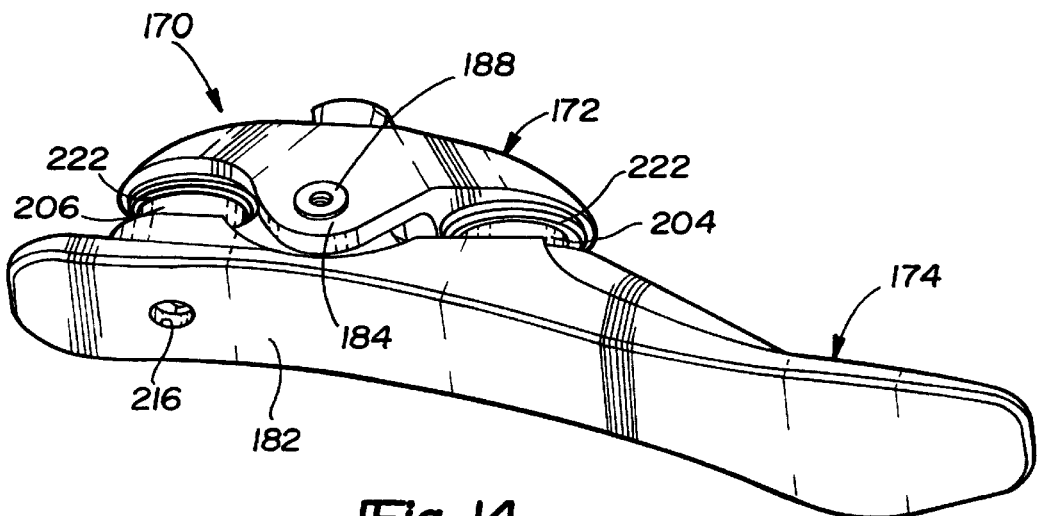
FIG. 14 is a side perspective view of the prosthetic foot assembly shown in FIG. 13.
Figure 23:
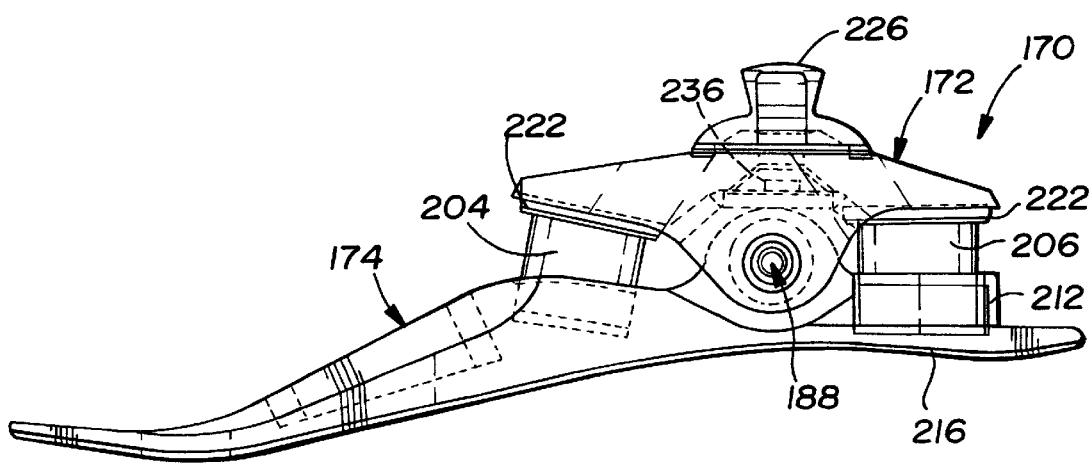
FIG. 23 is side elevational view of the prosthetic foot assembly of the present invention shown in FIG. 1.

Referring to FIGS. 13, 14, and 23, an alternative embodiment of a prosthetic foot assembly is generally shown at 170 and has a combination forefoot bone and heel bone defined herein as a "foreheel" 174 and an ankle member 172. The ankle member 172 has a top surface 176 and a bottom surface 178 and is pivotally connected to the foreheel member 174 through an axle joint 188. The foreheel member 174 has a top surface 180 and a bottom surface 182. The foreheel member 174 and the ankle member 172 are made from a suitable synthetic material such as a thermoplastic, e.g., a polyamide such nylon, or a composite material such as fiberglass reinforced graphite. The axle joint 188 provides for pivotal motion of the two members along the axis of the axle joint 188 which runs transverse to the longitudinal axis of the foot, i.e., the length of the foot. Additionally, as explained below, the axle joint 188 provides for limited torsional and/or pivotal motion about a direction transverse to the longitudinal axis of the axle 188. This is further described in Applicant's U.S. Pat. No. 5,158,570 issued Oct. 27, 1992, which has been incorporated by reference.

There are two resilient elements or cushions which cushion and resist rotation of the foreheel member 174 with respect to the ankle member 172. Resilient cushion 204 provides for resilient resistance of the foreheel member 174 with respect to the ankle member 172 against counterclockwise motion as referenced in FIG. 13. Resilient cushion 206 provides for resilient resistance of the foreheel member 174 with respect to the ankle member 172 against clockwise motion as referenced in FIG. 13. The cushions 204,206 can be selected by size and durometer to accommodate different weight, size and personal preferences of the user of the prosthetic foot assembly 170 and are preferably made from elastomers such as polyurethane. Additionally, the compressible element or cushion 120, described above, can be substituted for the cushions 204,206 shown in the Figures.

A sole 238 having specific shape can be affixed onto the foreheel member 174 preferably by the use of an adhesive. The sole 238 is preferably made from a neoprene crepe material and is sized to overhang the periphery of the bottom of the foreheel member 174 to allow both the sizing and the siding (right foot/left foot) of the prosthetic foot assembly 170.

The use of the sole 238 affixed to the foreheel member 174 allows for a commonly sized foot assembly 170 to be utilized for a range of differently sized feet by merely altering the amount of the sole 238 which overhangs the periphery of the bottom of the foreheel member 174. This feature is particularly beneficial when the foot assembly 170 is utilized for pediatric limb replacement. That is, as a child grows, rather than replacing the entire foot assembly 170, only the sole 238 needs to be replaced with a larger sole 238 in order to accommodate a larger sized prosthetic foot. This makes the foot assembly 170 more economical to the user.

The crepe neoprene material such as Soleflex, obtained from D&L Leather, Utica, N.Y., can also be used to lock the foreheel 174 into the cosmetic outer shell (not shown). In addition, the crepe neoprene material can add cushioning and can also be used to lock a sock (not shown) to the foot assembly 170.

Figure 15:
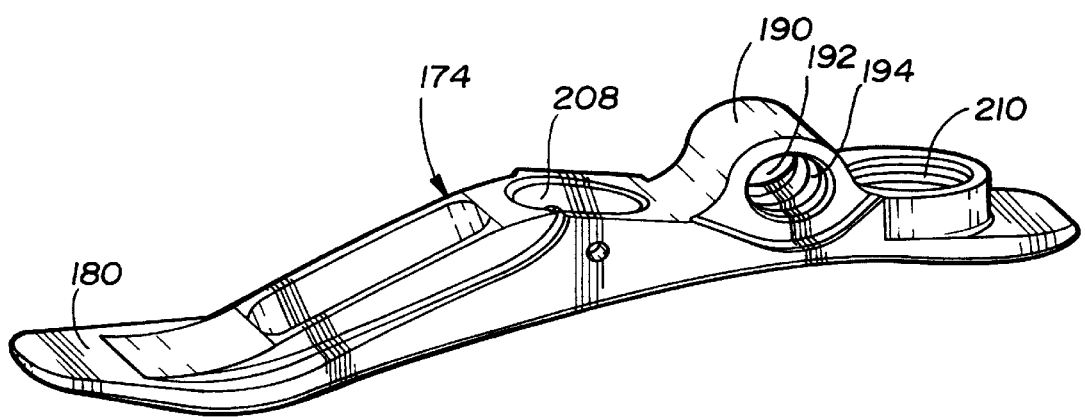
FIG. 15 is a perspective view from the side of a foreheel member.

Referring to FIG. 15, the axle joint 188 includes an axle or pin 200 having internally threaded ends positioned within the axle or pin 200 for receiving a threaded fastener 202. The fastener 202 can include a flange or washer to abut with the ankle member 172.

Referring to FIGS. 13, 14, 20, and 21, the ankle member 172 has two flange sections 184, each of which having an aperture 186 that receives the axle pin 200 therein. The flanges 184 are spaced apart to receive a central portion 190 of the foreheel member 174 therein.

Figure 16:
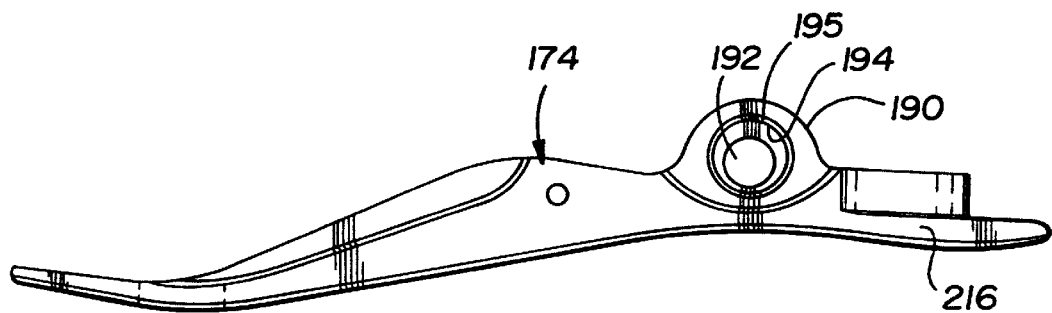
FIG. 16 is a side elevational view of the foreheel member of the present invention.
Figure 17:
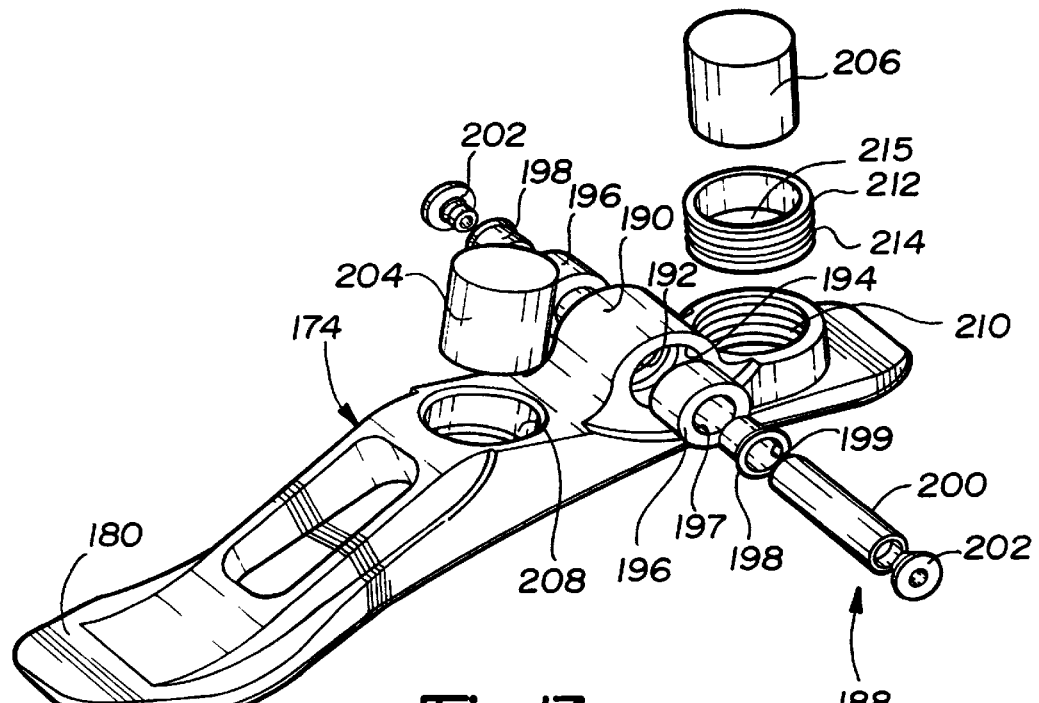
FIG. 17 is an exploded perspective view of the foreheel joint of the present invention.

Referring to FIGS. 15–19, the central portion 190 has a transverse bore 192 extending therethrough. Additionally, as best shown in FIGS. 15 and 16, concentrically aligned counterbores or recesses 194 are disposed in each side of the central portion 190 of the foreheel 174 for receiving and retaining two resilient bushings 196 therein. The bushings 196 can be made from an elastomeric material such as urethane such as that provided by Winfield Industries, Buffalo, N.Y. The elastomeric outer bushings 196 have an outer diameter sized to be snugly received in each counterbore 194. The concentrically disposed counterbores 194 constrain and absorb the lateral movement of the outer bushings 196 and provide for increased strength of the prosthetic foot assembly 170 under stress or use conditions as the top region 195 of the counterbores 194 is reinforced by being thicker at the point of maximal stress under stress loads transverse to the axle pin 200. Concentrically disposed within the bore 197 defined by each outer bushing 196 can be either a rigid inner bushing or sleeve 198 which snugly receives the axle pin 200 in a bore 199 as shown in FIG. 17. The inner bushings 198 are preferably constructed of a rigid material such as a metal including brass or titanium. Alternatively, instead of the inner bushings 198, a rigid sleeve can also be used. The rigid sleeve is preferably made of a metal such as brass.

The interfacing of the inner bushings or sleeve 198 with the outer bushings 196 acts to decouple each outer bushing 196 from the axle pin 200 eliminating what is known as compression/ratcheting failure. This phenomenon occurs during the gait cycle when the axle pin typically locks-up with the ankle member and the bushings lock-up with the heel member. The metal-to-metal interface of the inner bushings or sleeve 198 and the axle pin 200 prevents this phenomenon as the parts are able to slide relative to each other. Without creating this interface, the elastomeric outer bushings 196 would grab the axle pin 200 during relative rotation which stresses the elastomeric material leading to premature failure of the bushings 196 and also creates the potential to generate noise. Another benefit of this construction is the ability to assemble the parts without the need for lubricants, such as grease.

Figure 18:
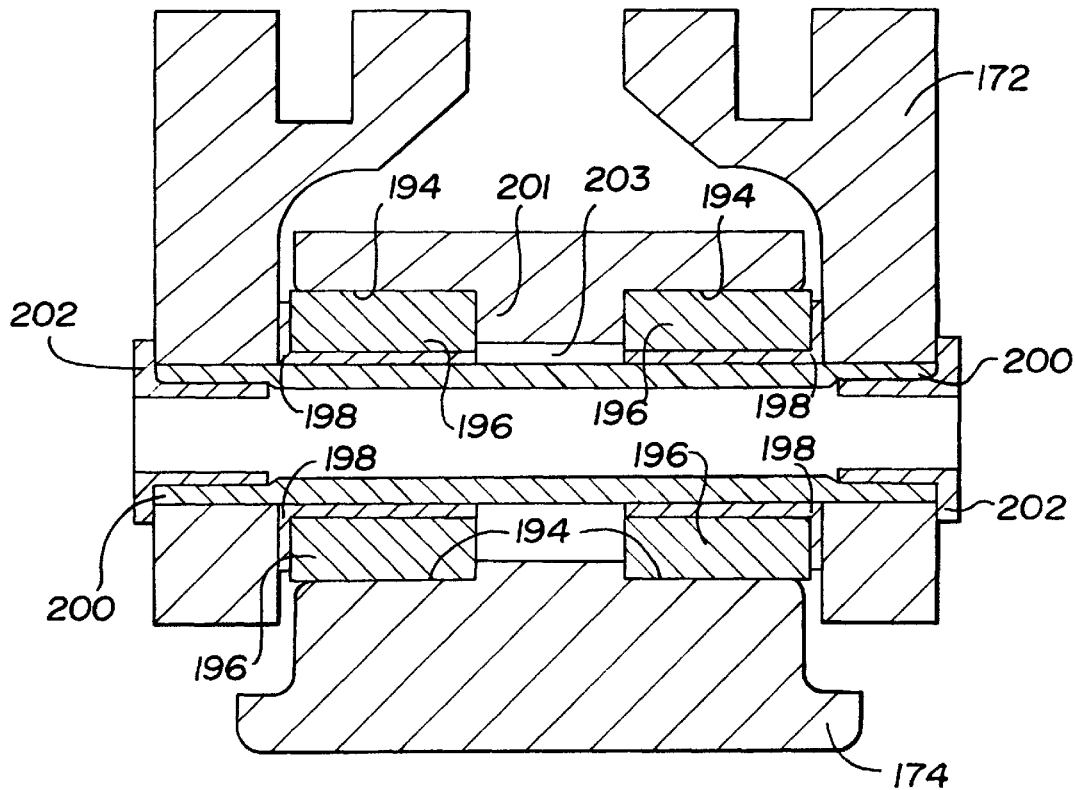
FIG. 18 is a cross-sectional view taken through a vertical plane of the ankle joint (ankle member and foreheel member) taken along line 18—18 of FIG. 13.

Referring to FIG. 18, an integral eccentric limiter bushing 201 is eccentrically disposed with respect to the bore 192 and limits the upward movement of the axle pin 200. That is, the bushing 201 limits motion that is transverse to the axis of axle pin 200. Since the bushing 201 is integral, it cannot slide or move laterally like prior art devices. As shown in FIG. 18, a gap 203 is disposed between the axle 200 and the eccentric limiter bushing 201 which allows the axle 200 to deflect giving greater side to side motion to the assembly 170 relative to the axle 200, while at the same time increasing the durability by limiting vertical or upward motion which is the direction in which the bushings 196 can be over-compressed.

Figure 19:
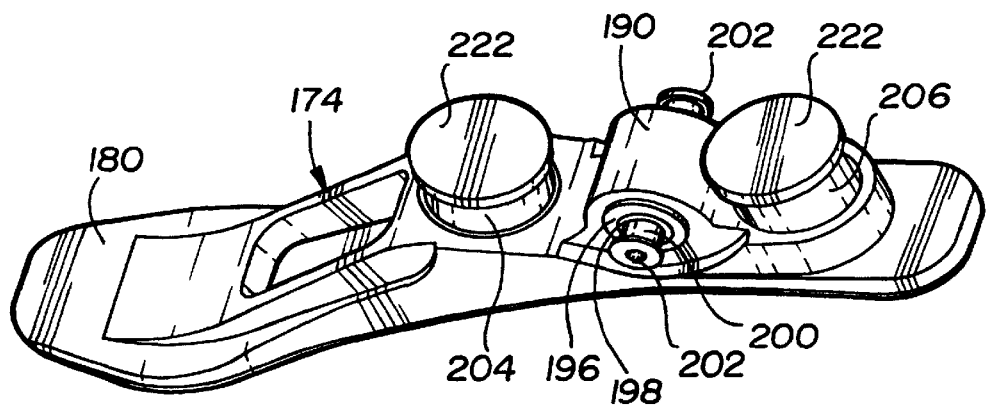
FIG. 19 is a perspective view from the top of the foreheel member of the present invention.

Referring to FIG. 19, the cushion 204 positively engages the foreheel member 174. This is accomplished by utilizing a recess 208 to provide controlled capture of the cushion 204. The cushion 206 is disposed in a cup 212 having a threaded outer surface 214 thereon and a hexagonally-shaped aperture 215. The cup 212 is threadingly disposed in a threaded recess 210 formed in the foreheel member 174. The recess 210 also includes a bore 216 extending through the bottom of the foreheel 174 as shown in FIG. 16. A hex-key tool can be inserted through the bore 216 to engage the aperture 215 in the cup 212 to allow for adjustment of cup 212 upwardly or downwardly to effect "preloading" of the foot assembly 170. This preloading allows for the slack in the foot assembly 170, due to compression of cushion 204 and 206, to be removed by upward and downward adjustment of the threaded cup 212. The placement of bore 216 allows for the foot assembly 170 to be adjusted or pre-loaded without removing the cosmetic outer layer (not shown) and also allows for the adjustment of the front 204 and rear 206 cushions to select the firmness or stiffness of foot assembly 170.

The cup 212 is preferably made of a metal material such as titanium or stainless steel. The foreheel member 174 which includes the threaded recess 210 therein is preferably formed of a thermoplastic material such as nylon. The threads disposed in the recessed 210 are preferably smaller than the threads disposed on the outer surface 214 of the cup 212 to create a locking-effect so that with normal action of the foot assembly 170, the foot assembly 170 does not loosen. Also, the locking-effect eliminates the need for additional components to maintain the adjustment of the foot assembly 170.

Figure 20:
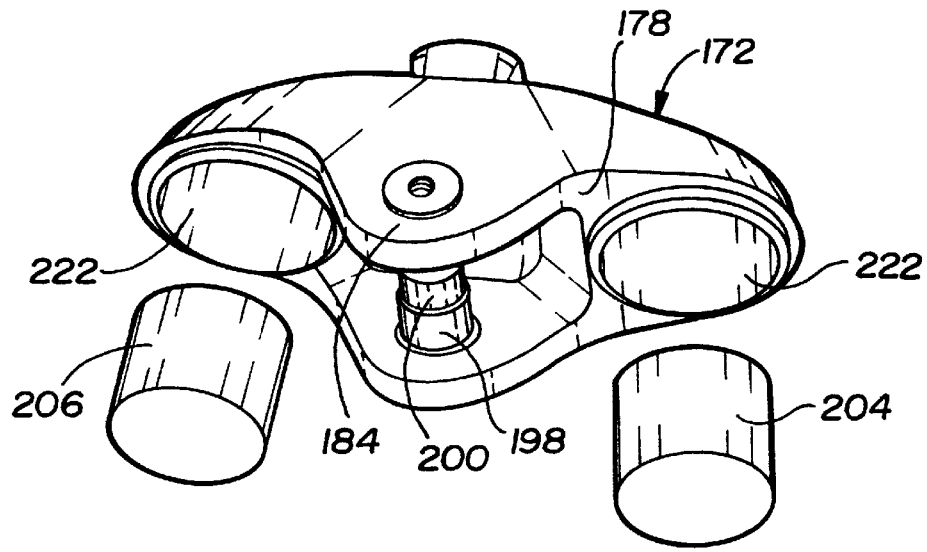
FIG. 20 is a perspective view from the bottom of the ankle member of the present invention.

Referring to FIGS. 19 and 20, buttons or discs 222 are disposed in recesses 220 in the ankle member 172. The buttons or discs 222 are preferably constructed of a material possessing a low coefficient of friction preferably such as an ultra-high molecular weight polyethylene (UHMWPE) or a fluoropolymer such as polytetrafluoroethylene (PTFE or TEFLON). The engagement of the elastomeric cushions 204,206 with the buttons or discs 222 facilitate the pre-loading function described above. Without the use of a button or discs 222 having a low coefficient of friction, the pre-loaded foot assembly 170 would be unable to rotate about the axle joint 188. That is, the button or discs 222 constructed of a low friction material, allows the ankle member 172 to slide across the cushions 204,206 which are fixed at their distal end to the foreheel member 174. The buttons or discs 222 can also be utilized with the embodiment shown in FIGS. 1–12.

Figure 21:
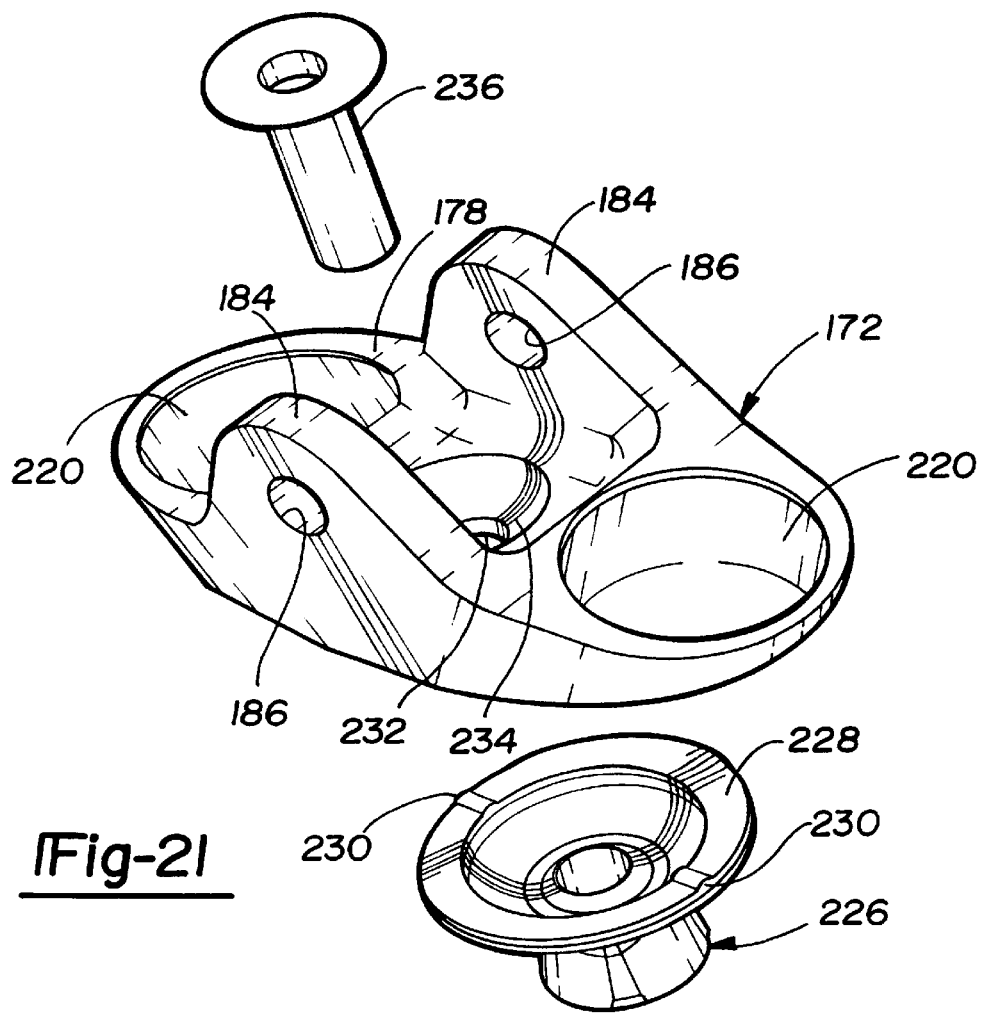
FIG. 21 is an exploded perspective view of the ankle member of the present invention.
Figure 22:
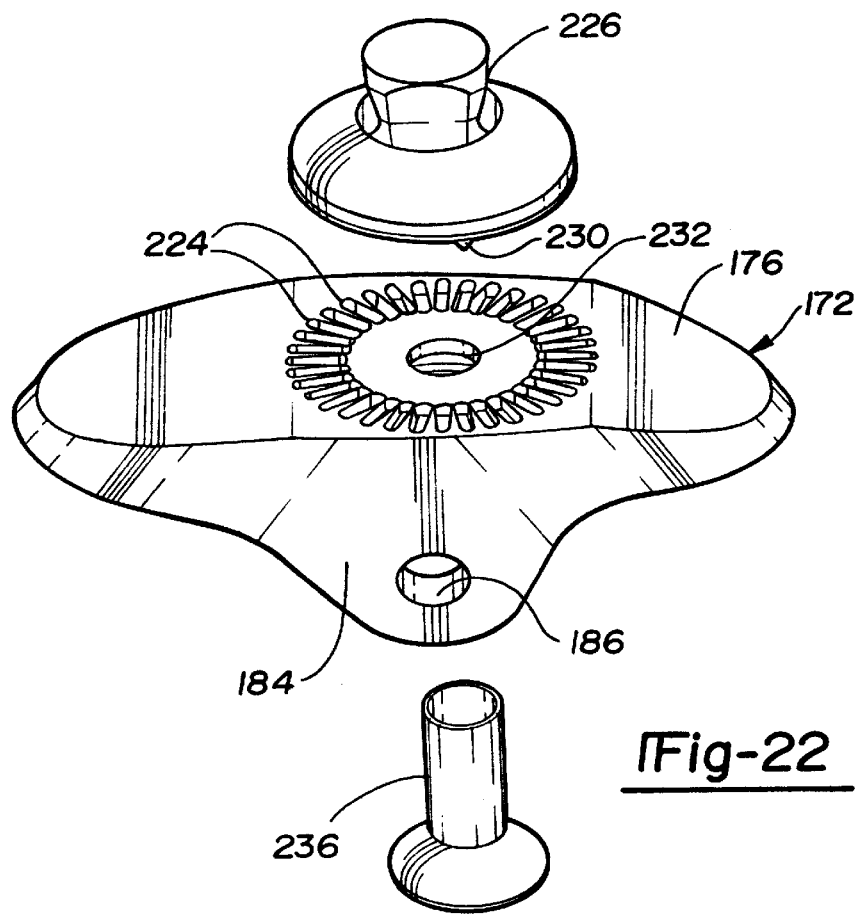
FIG. 22 is a perspective view from the side of the ankle member and adaptor of the present invention.

Referring generally to FIG. 13, a foot adaptor or integrated pyramid assembly 226 is shown. The adaptor or integrated pyramid assembly 226 is adaptable to be attached to endo-skeletal componentry (not shown). Exo-skeletal can be utilized by removing the assembly 226. Referring specifically to FIG. 21, the adaptor assembly 226 includes anti-rotation detents 230 disposed on its underside for engagement with the ankle member 172. A bore 232 is provided to receive a flat head cap screw 236 therein. The screw 236 is disposed in the bore 232 having a countersunk portion 234 disposed on the underside 228 of the ankle member 172. Referring to FIG. 22, the top surface 176 of the ankle member 172 is shown in greater detail specifically detailing the integrated adaptor or pyramid assembly 226 aspect of the ankle member 172. Indexing slots 224 are radially disposed about the aperture 232 and receive and retain the anti-rotation detents 230 disposed on the adaptor or pyramid 226 to allow for both indexing and fine radial adjustment of the assembly 170. The adaptor or pyramid assembly 226 is preferably constructed of a metal material such as titanium.

The use of the combination foreheel member (forefoot bone and heel) with a shape that allows for collapse of the arch combined with the specific placement of the pads 204,206 as described above, allow for the vertical excursion aspect of the joint and collapse of the arch in a prosthetic foot assembly 170 without the need for a third bone, i.e., separate forefoot and heel bones, thus decreasing the complexity and cost of the prosthetic foot assembly 170.

The present invention has been described in an illustrative manner. It is to be understood that the terminology which has been used is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. A prosthetic foot assembly, said assembly comprising:
an ankle member having shoulders extending from each side thereof, said shoulders each having an aperture therethrough;
a foreheel member having a top surface and a bottom surface pivotally connected to said ankle member by an axle;
said foreheel member having a central portion positioned between said shoulders of said ankle member, said central portion having a central transverse bore aligned with said apertures in said shoulders of said ankle member to form a passage through said foreheel member and said ankle member;
said central bore having a diameter larger than the diameter of said axle, said central bore having concentrically aligned counter-bores disposed in each side thereof;
a resilient bushing positioned in each counter-bore, each bushing having an aperture therethrough; and
a rigid liner positioned in the apertures of each resilient bushing, said rigid liner having a inner diameter sized to receive said axle, whereby said resilient bushings allow for resiliently resisted movement of said axle transverse to the longitudinal axis of said axle and said axle is decoupled from said ankle member.

2. A prosthetic foot assembly as set forth in claim 1, wherein said rigid liner is a bushing.

3. A prosthetic foot assembly as set forth in claim 1, wherein said rigid liner is a sleeve.

4. A prosthetic foot assembly as set forth in claim 1, wherein said inner diameter of said rigid liner snugly receives said axle therein.

5. A prosthetic foot assembly as set forth in claim 1 including an integral bushing eccentrically disposed in said central bore which limits upward vertical motion of said axle.

6. A prosthetic foot assembly as set forth in claim 1 further including a first compressible element disposed between said foreheel member and said ankle member forward of said central portion for resiliently resisting counterclockwise motion of said ankle member with respect to said foreheel member; and a second compressible element disposed between said foreheel member and said ankle member rearward of said central portion for resiliently resisting clockwise motion of said ankle member with respect to said foreheel member.

7. A prosthetic foot assembly as set forth in claim 6, wherein said first compressible element and said second compressible element are each received in a first recess and a second recess, respectively, disposed in said top surface of said foreheel member.

8. A prosthetic foot assembly as set forth in claim 7, wherein a portion of said second compressible element is received in a cup, said cup being received in said second recess.

9. A prosthetic foot assembly as set forth in claim 8, wherein said second recess is threaded.

10. A prosthetic foot assembly as set forth in claim 8, wherein said cup is threaded and is threadingly received in said second recess whereby said second compressible element can be adjusted upwardly and downwardly to pre-load the assembly or to adjust the firmness of the assembly.

11. A prosthetic foot assembly as set forth in claim 10, wherein a threaded fastener is disposed in said threaded second recess and extends into said second recess and engages said cup.

12. A prosthetic foot assembly as set forth in claim 6, wherein said ankle member includes a first recess and a second recess for receiving and retaining a low friction element therein.

13. A prosthetic foot assembly as set forth in claim 12, wherein each low friction element is positioned between said ankle member and one of said first compressible element and said second compressible element whereby under loading conditions, said ankle member is able to slide across said first and second compressible elements.

14. A prosthetic foot assembly as set forth in claim 6, wherein said ankle member includes a top surface adapted to engage an endoskeleton or an exoskeleton, said top surface of said ankle member having an aperture disposed therethrough; a plurality of slots radially disposed about said aperture; and a fastener disposed in said aperture for retaining an adaptor for affixation to an endoskeleton or an exoskeleton, said adaptor including at least one detent on its lower surface for engaging at least one of said radial slots to accommodate radial adjustment of the prosthetic foot assembly.

15. A prosthetic foot assembly as set forth in claim 6, wherein said bottom surface of said foreheel member includes a resilient material affixed thereto.

16. A prosthetic foot assembly as set forth in claim 15, wherein said resilient material extends beyond a periphery of said bottom surface of said foreheel member.

17. A prosthetic foot assembly as set forth in claim 15, wherein said resilient material is neoprene.

18. A prosthetic foot assembly as set forth in claim 6, wherein said first compressible element and said second compressible element have first and second substantially circular bearing surfaces, wherein a portion of each of said first and said second compressible elements spaced apart from one of said bearing surfaces has a smaller diameter than the diameter of at least one of said first and second bearing surfaces.

19. A prosthetic foot assembly as set forth in claim 18, wherein the diameter of said spaced apart portion is smaller than the diameter of said second bearing surface and larger than said first bearing surface.

20. A prosthetic foot assembly as set forth in claim 18, wherein the diameter of said spaced apart portion is smaller than the diameter of both said first bearing surface and said second bearing surface.

21. A prosthetic foot assembly as set forth in claim 18, wherein said spaced apart portion is a median portion of said compressible element, said median portion having a small diameter than the diameter of said first and said second bearing surfaces.

* * * * *